United States Patent
Pettersson et al.

(10) Patent No.: US 7,942,057 B2
(45) Date of Patent: May 17, 2011

(54) METHOD AND A SYSTEM FOR MONITORING STRUCTURAL CHANGES OF A FIBER WEB

(75) Inventors: Thorulf Pettersson, Täby (SE); Jan Lif, Hammarö (SE); Magnus Björklund, Karlstad (SE); Susanne Lindh, Avesta (SE)

(73) Assignee: Stora Enso AB, Falun (SE)

( * ) Notice: Subject to any disclaimer, the term of this patent is extended or adjusted under 35 U.S.C. 154(b) by 426 days.

(21) Appl. No.: 12/158,525

(22) PCT Filed: Dec. 20, 2006

(86) PCT No.: PCT/SE2006/050603
§ 371 (c)(1),
(2), (4) Date: Sep. 11, 2008

(87) PCT Pub. No.: WO2007/073340
PCT Pub. Date: Jun. 28, 2007

(65) Prior Publication Data
US 2009/0120190 A1    May 14, 2009

(30) Foreign Application Priority Data

Apr. 18, 2006 (SE) ........................... 0600857

(51) Int. Cl.
  *G01N 33/34* (2006.01)
  *G01N 29/37* (2006.01)
(52) U.S. Cl. ................. 73/598; 73/599; 73/602; 73/628
(58) Field of Classification Search ............ 73/598, 73/597, 599, 600, 602, 628, 643, 644
See application file for complete search history.

(56) References Cited

U.S. PATENT DOCUMENTS 4,938,404 A * 7/1990 Helms et al. ............... 226/10
4,976,150 A   12/1990 Deka
(Continued)

FOREIGN PATENT DOCUMENTS

| DE | 19905331 | 4/2000 |
| GB | 710124 | 6/1954 |
| WO | WO03095744 | 11/2003 |

OTHER PUBLICATIONS

International Search Report and International Preliminary Report on Patentability dated Aug. 2, 2007, which issued with respect to International Application No. PCT/SE2006/050603, upon which this application is based.

(Continued)

*Primary Examiner* — Jacques M Saint Surin
(74) *Attorney, Agent, or Firm* — Greer, Burns & Crain, Ltd.

(57) ABSTRACT

A method for monitoring the structural state of a fiber web (1) that is being processed by a fiber web processing machine comprising a fiber web processing station (2) is described. The method comprises the steps of arranging a generator (5) and a detector (6) of a generator-detector unit (4) on opposite sides of the traveling fiber web (1) downstream of the fiber web processing station; bringing the generator to emit an ultrasonic wave; bringing the detector to receive the ultrasonic wave; sending a signal representing the received ultrasonic wave to a control unit (10); and, in the control unit, analyzing the signal and extracting a value from the signal representing a measure of the received ultrasonic wave. A system for monitoring the structural state of a fiber web is also described.

13 Claims, 3 Drawing Sheets

U.S. PATENT DOCUMENTS

| | | | | |
|---|---|---|---|---|
| 5,274,573 A | * | 12/1993 | Buisker et al. | 702/103 |
| 5,652,388 A | * | 7/1997 | Callan et al. | 73/628 |
| 5,672,828 A | | 9/1997 | Allan | |
| 5,804,727 A | * | 9/1998 | Lu et al. | 73/597 |
| 5,814,730 A | * | 9/1998 | Brodeur et al. | 73/597 |
| 6,115,127 A | * | 9/2000 | Brodeur et al. | 356/503 |
| 6,668,231 B2 | * | 12/2003 | Stylios | 702/43 |
| 6,797,976 B2 | * | 9/2004 | Pechan et al. | 250/559.45 |
| 2002/0014120 A1 | | 2/2002 | Wunderer et al. | |

OTHER PUBLICATIONS

"En kritisk granskning av metoder för att detektera delaminering i papper," by Johan Persson, Abo akademi, kerniska tekniska fakulteten, 2000. (English Abstract at pp. 3-4).

"On the verification of the applicability of the orthtropic plate wave theory to paper," T. Pettersson, J. Anttila, Ultrasonics 39 (2002) pp. 617-622.

* cited by examiner

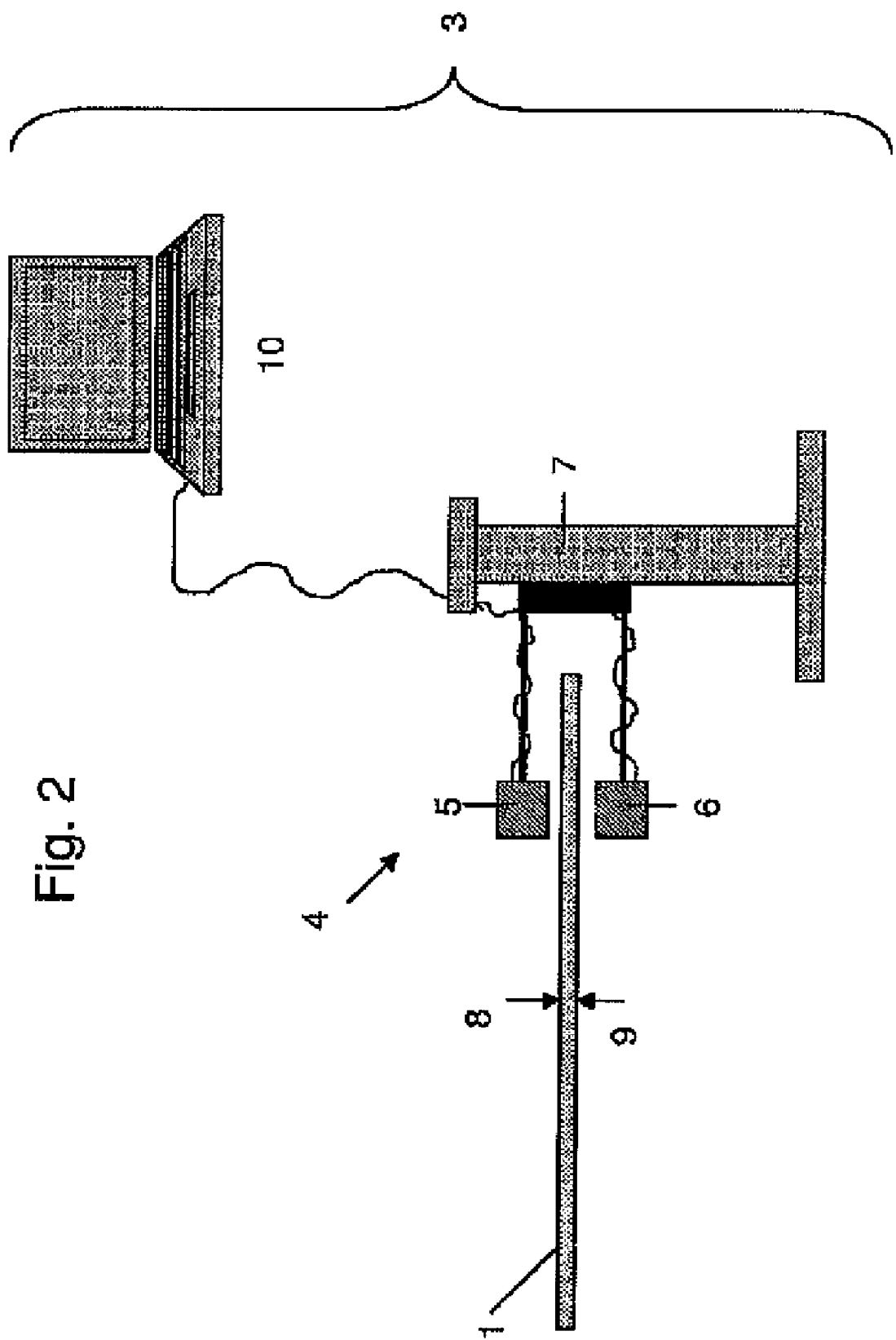

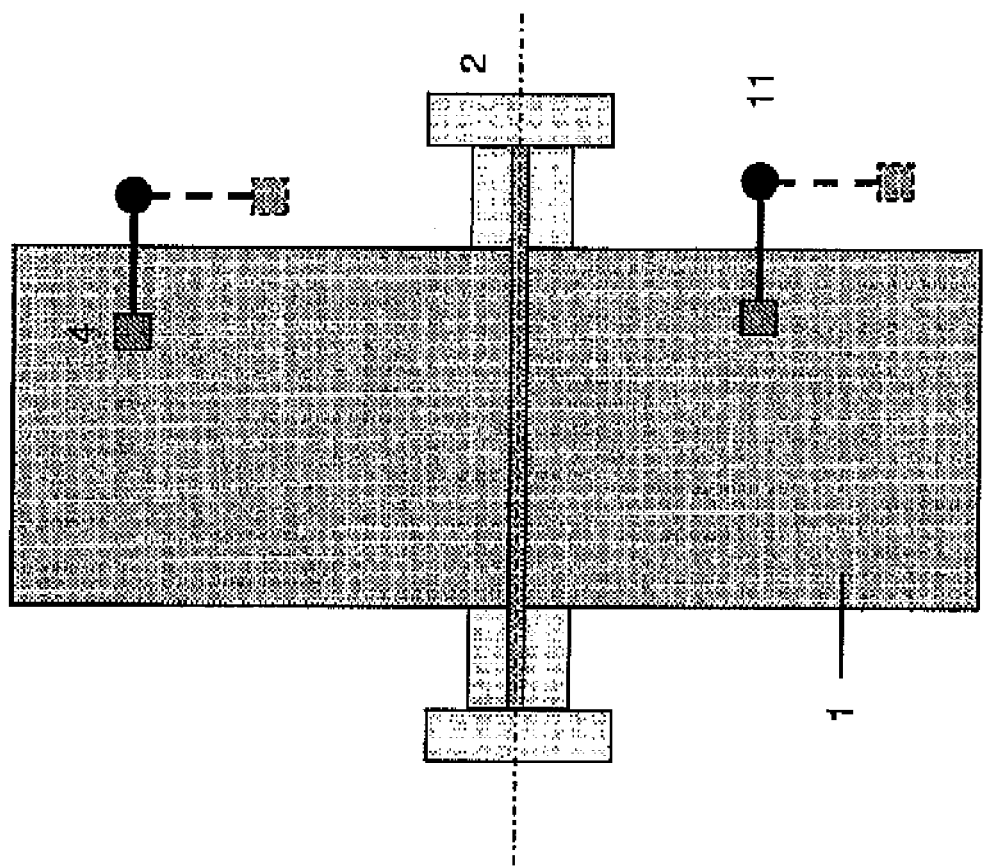

METHOD AND A SYSTEM FOR MONITORING STRUCTURAL CHANGES OF A FIBER WEB

This invention relates to a method for detecting structural changes in the thickness direction of a porous material, for example paperboard or paper.

Specifically, the invention relates to a method for monitoring the structural state of a fiber web that is being processed by a fiber web processing machine comprising a fiber web processing station, and also to a system for monitoring the structural state of a traveling fiber web that is processed in a fiber web processing machine comprising a fiber web processing station, which system comprises a generator-detector unit and a control unit that is configured to receive a signal from the generator-detector unit.

The method can be used to determine the structural changes of sheets or moving webs, both off-line and on-line during manufacturing or subsequent process steps.

The invention also relates to manufacturing of paperboard- and paper based products that have been quality-controlled by the method.

BACKGROUND OF INVENTION

During converting operations, e.g. fiber web processing machine operations, of paperboard or paper, such as decurling, sheeting, cutting, creasing, pigment coating, polymer coating, printing, decurling, varnishing or embossing, structural changes such as delamination and pigment coating cracks can initiate. Delamination can also occur during the production process of paperboard or paper, for example during wet pressing, drying or calendering. Delamination occurs when the applied load on the paperboard or paper exceeds the strength of the material. The fibers in the paperboard or paper will then be locally separated; this will create a new configuration of the fiber network and new free surfaces inside the material. The end user may then notice a reduced internal strength as the paperboard or paper is exposed to a new set of external loads. If the paperboard consists of several layers, it is also possible that the layers will be separated; this which also results in structural changes such as delamination and decreased internal strength. Internal strength reduction can cause runability or quality problems for the next fiber web processing step, e.g. printing, creasing, folding and lamination. If the paperboard or paper is pigment coated and the applied external load is too large, the coating can crack which will create an uneven surface of the product. Coating cracks strongly influence the printing properties of the product, which are very dependent on a smooth surface.

Both delamination, coating cracks and other structural changes such as light scattering changes are often difficult to detect visually or with standard laboratory test methods. In the diploma work "En kritisk granskning av metoder för att detektera delaminering i papper" by Johan Persson, ÅBO AKADEMI, KEMISKA TEKNISKA FAKULTETEN, 2000, the insufficiency of different methods for measuring delamination is discussed. One method used for measuring strength properties in the thickness direction, often referred to as z-direction (ZD), of paperboard or paper products is z-strength testing. Another method is Scott-Bond. However, these methods are destructive and do not indicate where delamination or weakened zones are located because the commonly used test frequency is very low. They only show that the strength of the paperboard or paper has decreased. There are also several other methods that can be used, i.e. peeling, light scattering or permeability tests like Gurley. Common among all those methods is that they are not sensitive enough to measure millimeter size delaminations or small coating cracks. Today, structural changes are commonly detected visually during regular production; this approach is subjective as it depends on the person inspecting the material. The inspected part of the material is also very limited, i.e. damaged material can pass the process.

Traditional treatment and analysis techniques are based on the evaluation of elastic properties by means of in-plane ultrasonic waves applied to paper sheets or webs. One example is described in WO03095744.

WO03095744 describes a method and an apparatus for online monitoring of a paper sheet during production. According to the method, a laser generator generates and directs a laser beam at the paper sheet as it travels through the production process. As the laser beam impinges the paper sheet, in-plane ultrasonic waves are generated. A second laser generator is used to generate and direct a second laser beam at the paper sheet. The second laser beam is reflected from the paper sheet with a modulated characteristic associated with the sonic waves propagated in the plane. An interferometer is used to measure at least a part of the second laser beam as it is reflected from the paper sheet. The interferometer may then send a signal to a distributed control system, which may implement an action such as changing production process parameters.

The method according to WO03095744 thus utilizes in-plane propagation of sound waves in paper sheets. However, the article *On the verification of the applicability of the orthtropic plate wave theory to paper*, T. Pettersson, J. Anttila, Ultrasonics 39 (2002) 617-622, describes an alternative interpretation of the theory on sound wave propagation through a porous material such as paper. According to the article, when applying ultrasonic waves to a paperboard the so-called X mode wave was found to propagate in the thickness direction (ZD) of the paperboard; this is contrary to previous beliefs. According to the invention, this finding on the direction of propagation of the X mode wave is utilized to achieve a new and improved method for detection of structural changes in a porous material such as paper, paperboard or board.

SUMMARY OF THE INVENTION

The method according to the invention is characterized by the steps of:
  downstream of the fiber web processing station, arranging a generator and a detector on opposite sides of the traveling fiber web of a generator-detector unit;
  bringing the generator to emit an ultrasonic wave;
  bringing the detector to receive the ultrasonic wave;
  sending a signal representing the received ultrasonic wave to a control unit;
  in the control unit, analyzing the signal and extracting a value from the signal representing a measure of the received ultrasonic wave.

The system according to the invention is characterized in that the generator-detector unit comprises:
  a generator positioned on one side of the traveling fiber web downstream of the fiber web processing station, the generator being configured to emit an ultrasonic wave; and
  a detector positioned on the opposite side of the traveling fiber web downstream of the processing station; the detector being configured to receive the ultrasonic wave after the wave has propagated through the traveling fiber web, wherein the signal received by the control unit is a signal representing the ultrasonic wave received by the detector and wherein the control unit is configured to analyze the signal and extract a value from the signal representing a measure of the received ultrasonic wave.

According to the invention, the X mode is used as a measure of the structural state in a porous material, such as paperboard or paper. A change in the intensity level of the X mode is used as a measure of structural changes.

BRIEF DESCRIPTION OF THE DRAWINGS

For a more complete understanding of the present invention and advantages thereof, reference is made to the following description taken in conjunction with the accompanying drawings in which the reference numbers in the text relate to corresponding features in the drawings.

FIG. 2 describes a part-view of the monitoring system according to FIG. 1.

FIG. 3 describes a part-view of a fiber web processing machine comprising a monitoring system according to a second embodiment of the invention.

DETAILED DESCRIPTION OF THE PREFERRED EMBODIMENT

Figure 1:
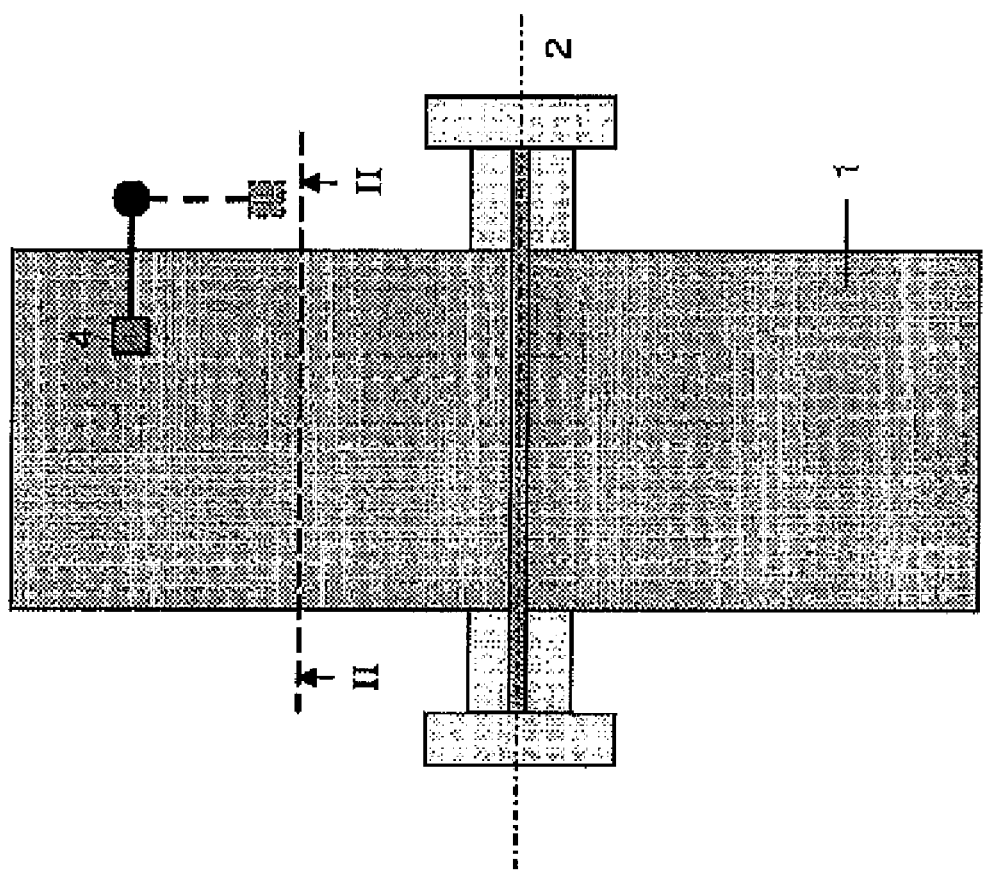
FIG. 1 describes a part-view of a fiber web processing machine comprising a monitoring system according to a first embodiment of the invention.

FIG. 1 shows a part-view of a machine for processing a fiber sheet or web 1, i.e. a sheet or web of paper, paperboard or board. In this case the fiber web processing machine is a sheet cutter comprising a decurling unit, i.e. a machine converting paper or paperboard by cutting a continuous web to sheets.

The fiber web processing machine comprises a station 2 for processing the web 1, the processing station 2 being a decurling unit for correcting curling defects in the web 1. The fiber web processing machine also comprises a monitoring system 3 according to the invention, the system 3 being arranged to analyze the traveling web 1 in conjunction with the processing station, i.e. the decurling unit 2, in order to discover structural changes in the fiber web 1. Structural changes can be caused by changed running conditions in the fiber web processing machine or in some earlier processing station or by unknown process disturbances during manufacturing.

FIG. 2 shows the monitoring system 3 and the traveling web 1 in a view along the section labeled II-II in FIG. 1. The system 3 comprises an acoustic generator-detector unit 4 being arranged downstream of the decurling unit 2 adjacent to the path of travel of the web 1. The generator-detector unit 4 comprises an acoustic generator 5 that is arranged on one side of the traveling web 1. Preferably, a non resonant generator and detector are used which provides low "ringing", i.e. short dead times. The generator-detector unit 4 also comprises an acoustic detector 6 that is arranged on the opposite side of the traveling web 1. The generator 5 and detector 6 are aligned along the acoustic axis of generator-detector unit 4. The generator-detector unit 4 is arranged so it is perpendicular to the traveling web 1, i.e. the incidence angle to the traveling web 1 is preferably close to zero (0°). The distance between the generator 5 and the detector 6 is such that an acoustical interference free zone between the generator 5 and the detector 6 exists. The generator 5 and detector 6 are mounted on a stand 7. In order to simplify web threading, the generator-detector unit 4 can be swung aside as is indicated by the dashed lines in FIG. 1. Alternatively, the generator and detector can be mounted on a measurement frame in such a way that the lateral position of the generator-detector unit can be adjusted, e.g. by traversing so that the entire paperboard web is covered in the cross direction (CD).

The monitoring system 3 also comprises a control unit 10, which preferably is implemented on a computational circuitry, computer or workstation. The control unit 10 is arranged to receive signals from detector 6. Control unit 10 can control the generator 5, e.g. turn it on and off.

When in operation, the acoustic generator 5 emits an ultrasonic wave. The ultrasonic wave has a frequency preferably between 100-800 kHz. The used frequency is chosen in such way that the X mode can propagate in the thickness direction of the actual type of material i.e. it is a frequency where the X mode exists in the material, as described in *On the verification of the applicability of the orthtropic plate wave theory to paper*, T. Pettersson, J. Anttila, Ultrasonics 39 (2002) 617-622. The chosen sine wave can be continuous, pulsed or frequency modulated. The ultrasonic wave travels through the air and in the thickness direction (ZD) through the paperboard and is detected on the opposite side of the traveling paperboard by the detector 6. A signal representing the detected wave is sent to the control unit 10 where the intensity, i.e. the intensity or amplitude of the X mode wave is registered as an X mode signal value, e.g. a voltage value. The control unit 10 is thus arranged to extract a value from the X mode signal, preferably a numerical value, and the value representing a measure of the received ultrasonic wave. The X mode signal value is compared to previously detected X mode signal values and any discovered difference is thus a measure of structural changes in the paperboard. This information can be used to adjust the various settings of the decurling unit 2 or to adjust other processing parameters of the sheeting machine.

The monitoring system can also be equipped with two or more generator-detector units for detecting structural changes. FIG. 3 shows the fiber web processing machine of FIG. 1 having a second generator-detector unit 11 being arranged upstream of the decurling unit 2. The second generator-detector unit 11 is practically identical to the first generator-detector unit 4, and the control unit 10 is arranged to receive signals from the detector of the second generator-detector unit 11 as well. The signals from the generator-detector units 4, 11 are sent to the control unit 10 which treats the signals from both generator-detector units 4, 11 in the same way and extracts values from the signals. The extracted values represent values of the X mode of the received signals from the ultrasonic waves. The X mode signal value derived from the downstream detector 6 is then compared to the X mode signal value derived from the upstream detector. By comparing the values, structural changes of the paperboard due to the workings of the decurling unit 2 can be identified. This information can then be used to adjust the settings of the decurling unit 2. The two generator-detector units 4 and 11 allow for spatial synchronization resulting in an improved sensitivity of the method and the possibility to determine both the size and the location of the structural change. Spatial synchronization meaning that the two generator-detector units are arranged at the same lateral (CD) position, i.e. the generator-detector units are arranged along the same path. And that the X mode signals are time shifted before they are compared so that the comparison is done on values originating from the same measured area of the traveling web.

A trial with a single generator-detector unit arrangement placed after a decurling station was conducted. The decurling station was arranged to produce flattened sheets from paperboard rolls by removing curl tendency of the sheets. This was performed by mechanically loading the paperboard in a nip passage. The speed of the moving web was between 100 and 200 meters per minute, the frequency used was 200 kHz and the sampling rate was 67 Hz. The results show that the monitoring system can detect both internal board damage and coating cracks. This was observed by correlating higher and lower measured X mode signal levels. It was found that a reduced X mode signal level corresponds to reduced strength properties (delamination) and that an elevated X mode signal corresponds to damages to the pigment coating (cracks).

The two different kinds of damages, delamination and surface cracks, can occur at the same time. As stated before, the two different kinds of damage produce either a higher or lower signal value of the received X mode. Due to the different characteristics of the two damage types they can be separated by X mode signal analysis. The cracks are very small and distinct and the X mode signal change to a higher level will have the same distinctiveness whilst the delamination damage is larger and builds up more gradually and thus a smoother change to a lower value of the X mode signal is observed.

Example 1

A trial with 250 gsm paperboard shows that the level of the X mode signal agrees with internal damages of the paperboard. The z-directional strength value (z-strength and Scott-Bond) becomes lower with lower X mode signal level. The z-strength was measured according to SCAN-P80:98 and the Scott-Bond were measured according to TAPPI 569 (Huygen). Prior to testing, the test pieces were conditioned at 23° C./50% RH. Visual inspection was done by experienced personnel and at low incident angle light. The test piece was controlled both in a flat and in a curled state. Delamination was observed as a local bubble on a curled sample.

| Fully coated CTMP board, 250 gsm | Reference of the material | Unit step Setting 1 | Unit step Setting 2 | Unit step Setting 3 |
|---|---|---|---|---|
| X mode signal level (mV) | 440 | 375 | 275 | 225 |
| Visual judgment* | No visual damages | No visual damages | Delamination | Delamination |
| Z-strength (kPa) | 343 | 273 | 236 | 226 |
| Scott-Bond (J/m$^2$) | 195 | 194 | 130 | 127 |

*Visual inspection was done by the laboratory technician

Example 2

A trial with 350 gsm paperboard shows that a higher level of the X mode signal corresponds to surface cracks. The z-strength was measured according to SCAN-P80:98. Prior to testing, the test pieces were conditioned at 23° C./50% RH. Visual inspection was done by experienced personnel and at low incident angle light. The test piece was controlled both in a flat and curled state. Surface cracks were observed as small (<10 μm) surface creases on a flat sample.

| Fully coated CTMP board with coated reverse, 350 gsm | Reference value of the material | Unit step Settings 4 | Unit step Settings 5 |
|---|---|---|---|
| X mode signal level (mV) | 105 | 130 | 105 |
| Visual judgment* | No visual damages | Surface cracks | No visual damages |
| Z-strength (kPa) | 390 | 230 | 366 |

*Visual inspection was done by the laboratory technician

The monitoring system according to the invention can be used on-line, i.e. during regular production of paper, paperboard and board, or during subsequent processing of the fiber web, e.g. decurling or rewinding. Examples of processing stations where the system can be implemented are a drying section and a press section of a paper, paperboard or board machine. The monitoring system can also be used during calendering, pigment coating, polymer coating, printing, decurling, cutting, creasing, sheeting, varnishing or embossing. In fact, the system and the method of the invention can be used in all kinds of possible processing stations in a fiber web producing machine, or in processing stations in a subsequent fiber web processing machine, where the loading of the fiber web may cause permanent structural changes of the fiber web.

The system can be used for on-line or off-line quality control. The system can for example be used as laboratory equipment measuring the structural state of sheets. The system can be used on a traveling fiber web or on a static fiber web.

The method can be used for all porous sheet and web materials where structural changes are expected.

Paperboard refers to all common board products such as liquid board, grey board, carton board, folding box board, general packaging board, graphical boards, cigarette board, pharmaceutical board, core boards or liner board.

In view of the above detailed description of the present invention and associated drawings, other modifications and variations will become apparent to those skilled in the art. However, it should be apparent that such other modifications and variations may be effected without departing from the spirit and scope of the invention.

The invention claimed is:

1. A method for monitoring the structural state of a fiber web that is being processed by a fiber web processing machine comprising a fiber web processing station, said method comprising:
   downstream of the fiber web processing station, arranging a generator and a detector on opposite sides of the traveling fiber web of a generator-detector unit;
   bringing the generator to emit an ultrasonic wave;
   bringing the detector to receive the X-mode of the ultrasonic wave that has propagated through the traveling fiber web;
   sending a signal representing the received X-mode to a control unit;
   in the control unit, analyzing the signal and extracting a value from the signal representing a measure of the received X-mode.

2. The method according to claim 1, further comprising the step of correlating said value with a known structural state of the fiber web.

3. The method according to claim 1, further comprising comparing said value with values extracted from X-modes previously received by the detector.

4. The method according to claim 1, further comprising:
upstream of the fiber web processing station, arranging a generator and a detector on opposite sides of the traveling fiber web of a second generator-detector unit;
bringing the generator of the second generator-detector unit to emit an ultrasonic wave;
bringing the detector of the second generator-detector unit to receive the X-mode of the ultrasonic wave that has propagated through the traveling fiber web emitted by the generator of the second generator-detector unit;
bringing the detector of the second generator-detector unit to send a signal representing the received X-mode to the control unit;
in the control unit, analyzing the signal representing the X-mode received by the detector of the second generator-detector unit and extracting a value from the signal representing a measure of the received X-mode.

5. The method according to claim 4, further comprising the step of comparing the value derived from the downstream detector to the value derived from the upstream detector.

6. A fiber web controlled by the method according to claim 1.

7. A system for monitoring the structural state of a traveling fiber web that is processed in a fiber web processing machine comprising a fiber web processing station, which system comprises:
a generator-detector unit; and
a control unit that is configured to receive a signal from the generator-detector unit,
wherein the generator-detector unit comprises:
a generator positioned on one side of the traveling fiber web downstream of the fiber web processing station, the generator being configured to emit an ultrasonic wave; and
a detector positioned on the other side of the traveling fiber web downstream of the fiber web processing station, the detector being configured to receive the X-mode of the ultrasonic wave that has propagated through the traveling fiber web,
wherein the signal received by the control unit is a signal representing the X-mode received by the detector and wherein the control unit is configured to analyze the signal and extract a value from the signal representing a measure of the received X-mode.

8. The system according to claim 7, wherein said value is correlated with a known structural state of the fiber web.

9. The system according to claim 7, wherein said value is compared to values derived from X-modes previously received by the detector.

10. The system according to claim 7, further comprising:
a generator of a second generator-detector unit positioned on one side of the traveling fiber web upstream of the processing station, the generator being configured to emit an ultrasonic wave; and
a detector of the second generator-detector unit positioned on the opposite side of the traveling fiber web upstream of the processing station, the detector of the second generator-detector unit being configured to receive the X-mode of the ultrasonic wave originating from the generator of the second generator-detector unit after the ultrasonic wave has propagated through the traveling fiber web,
wherein the control unit is configured to receive a signal from the detector of the second generator-detector unit, this second signal representing the X-mode received by the detector of the second generator-detector unit, and wherein the control unit is configured to analyze the second signal and extract a value from the second signal representing said measure of the received X-mode.

11. The system according to claim 10, wherein the value derived from the downstream detector is compared to the value derived from the upstream detector.

12. A fiber web processing machine comprising a system according to claim 7.

13. The machine according to claim 12, further comprising a decurling station being monitored by said system.

* * * * *